United States Patent
Jennings

(10) Patent No.: US 10,675,171 B2
(45) Date of Patent: Jun. 9, 2020

(54) PANNUS SUPPORT DEVICE, SYSTEM AND METHOD

(71) Applicant: Angela Jennings, Schenectady, NY (US)

(72) Inventor: Angela Jennings, Schenectady, NY (US)

(*) Notice: Subject to any disclaimer, the term of this patent is extended or adjusted under 35 U.S.C. 154(b) by 863 days.

(21) Appl. No.: 15/237,314

(22) Filed: Aug. 15, 2016

(65) Prior Publication Data

US 2017/0042718 A1    Feb. 16, 2017

Related U.S. Application Data

(60) Provisional application No. 62/205,496, filed on Aug. 14, 2015.

(51) Int. Cl.
*A61F 5/03*    (2006.01)
*A61F 5/02*    (2006.01)

(52) U.S. Cl.
CPC . *A61F 5/03* (2013.01); *A61F 5/02* (2013.01)

(58) Field of Classification Search
CPC ...... A61F 5/03; A61F 5/02; A61F 5/30; A61F 5/24; A61F 5/26; A61F 5/28; A41C 3/00
See application file for complete search history.

(56) References Cited

U.S. PATENT DOCUMENTS

| | | | |
|---|---|---|---|
| 284,831 A | 9/1883 | Galny | |
| 1,068,268 A * | 7/1913 | Patterson | A41C 1/10 450/113 |
| 1,828,015 A * | 10/1931 | Allebach | A41C 1/10 450/113 |
| 2,250,807 A | 7/1939 | Lunney | |
| 4,421,117 A * | 12/1983 | Klausen | A41C 1/10 450/131 |
| 4,497,071 A * | 2/1985 | Bell | A41D 1/08 2/94 |
| 4,789,372 A * | 12/1988 | Wicks | A41C 1/10 2/44 |
| 5,702,286 A | 12/1997 | Seering et al. | |
| 5,897,423 A * | 4/1999 | Rosenberg | A41C 1/10 450/115 |
| 5,928,059 A * | 7/1999 | Wicks | A41C 1/10 2/408 |
| 6,846,220 B2 | 1/2005 | Wakefield | |
| 7,008,292 B2 | 3/2006 | Cosentino et al. | |
| 7,988,527 B2 * | 8/2011 | Christensen | A61F 5/03 128/99.1 |
| 8,113,911 B1 * | 2/2012 | Hansen | A41D 1/21 450/155 |
| 8,764,691 B2 | 7/2014 | Sharps et al. | |

* cited by examiner

Primary Examiner — Tarla R Patel
(74) Attorney, Agent, or Firm — Schmeiser, Olsen & Watts, LLP

(57) ABSTRACT

Disclosed herein is a pannus support device that includes a pannus pouch configured to receive an abdominal panniculus of a wearer that is extending to cover at least a portion of the thigh, a shoulder support structure, and at least one strap connecting the pannus pouch to the shoulder support structure. The shoulder support structure, the at least one strap and the pannus pouch are configured to distribute the weight of the abdominal panniculus to the shoulders of the wearer and off at least the portion of the thigh of the wearer. Further disclosed is a system including a removable pannus pouch liner, and a method of distributing the weight of the abdominal panniculus.

18 Claims, 4 Drawing Sheets

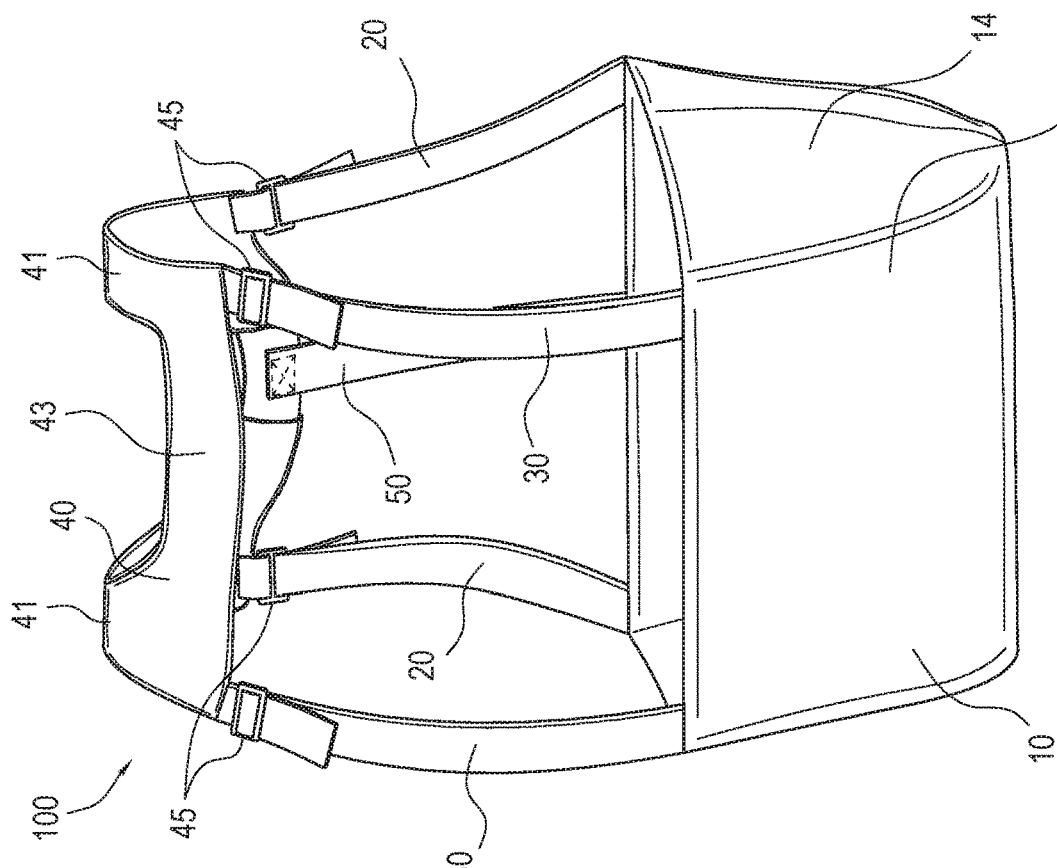
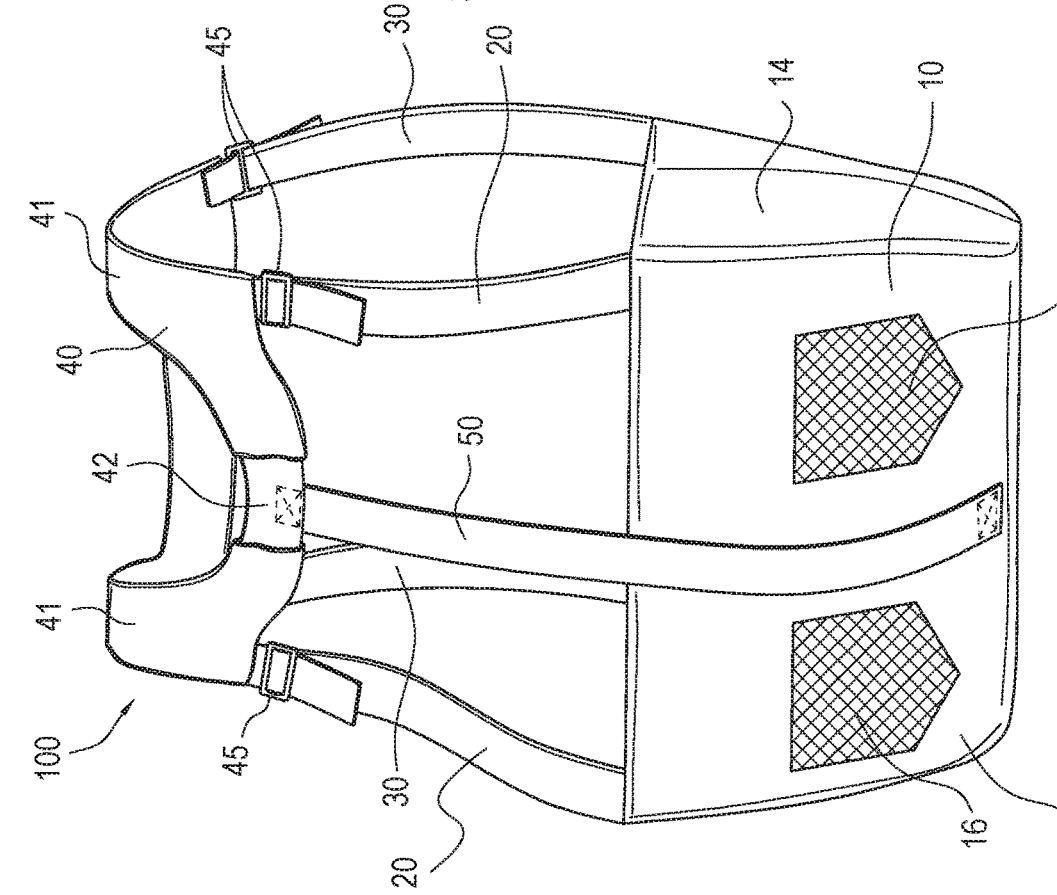

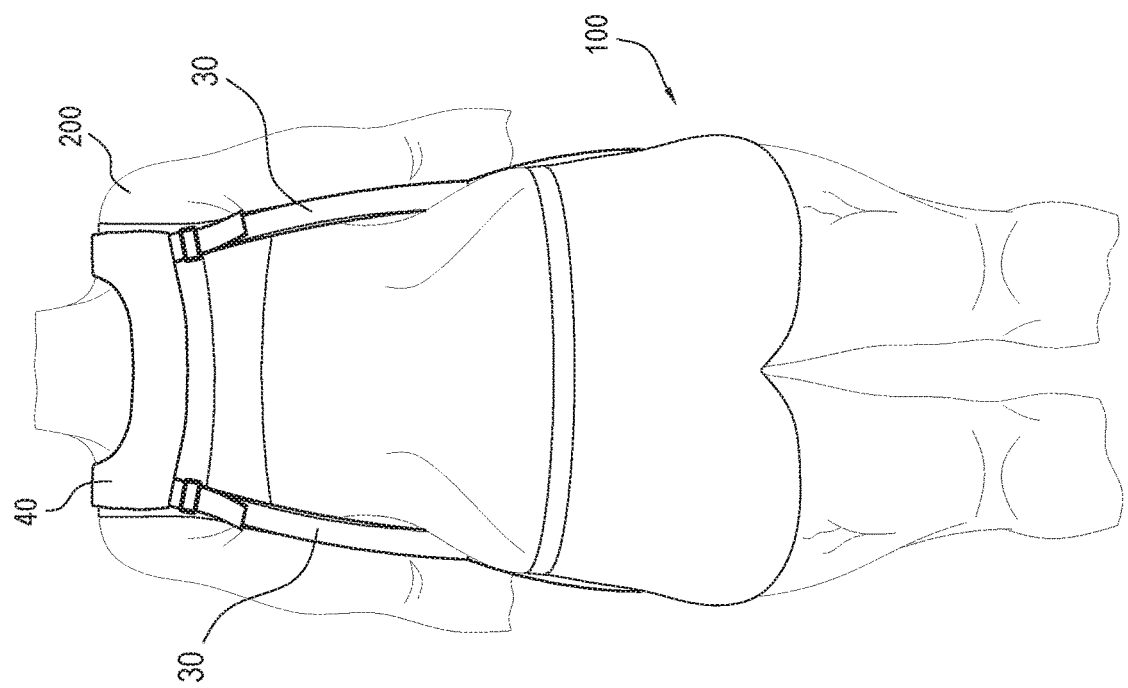
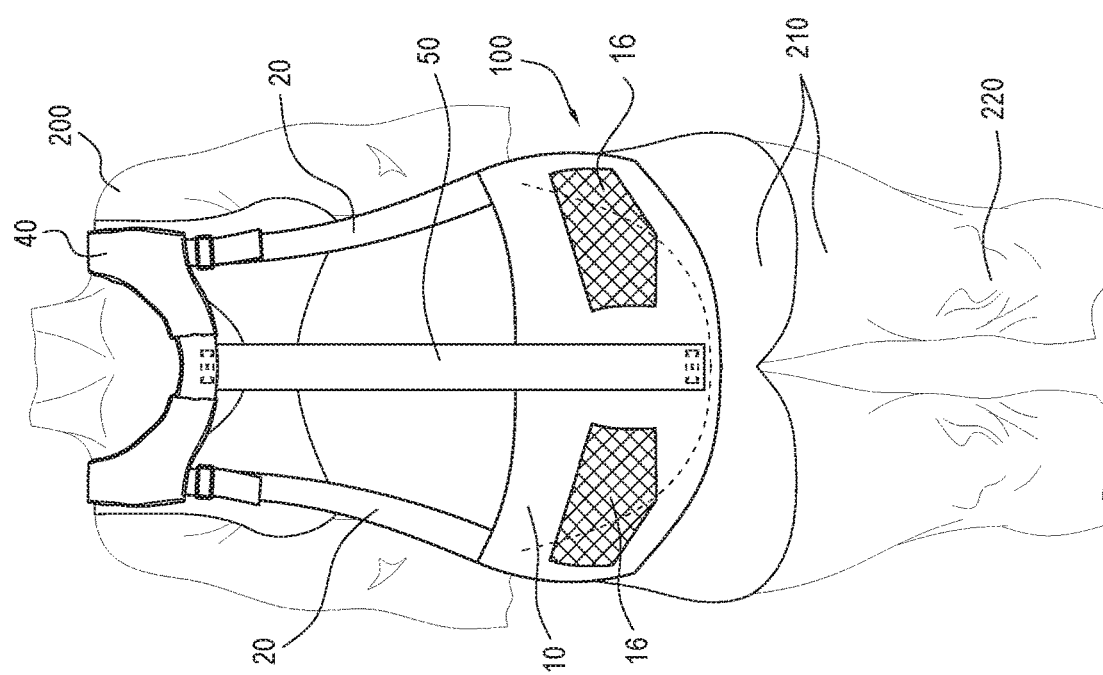

ated of the thigh of the wearer.

PANNUS SUPPORT DEVICE, SYSTEM AND METHOD

CROSS-REFERENCE TO RELATED APPLICATIONS

This application claims priority to provisional application No. 62/205,496, having a filing date of Aug. 14, 2015, the entire contents of which are hereby incorporated by reference.

FIELD OF THE TECHNOLOGY

The subject matter disclosed herein generally relates to a support for an abdominal panniculus or pannus. More particularly, the invention provides an device which may provide an individual with an increased range of motion by supporting the individual's pannus.

BACKGROUND

Overweight or obese individuals often struggle with ambulating or walking, along with other physical activities. For example, individuals may be limited in their endurance or even in their ability walk short distances. These difficulties may be due to the excess amount of weight carried or to a general lack of wellness. However, some individuals may struggle with movement not because they are not physically strong enough to move their body, but rather because the presence of extra tissue impedes their motions.

This tissue may be primarily fatty tissue or it may be any other type of tissue. The tissue may be referred to as abdominal panniculus, or pannus. For the purposes of this disclosure, these two terms are considered equivalent and are used to refer to the same element, namely a layer of fatty tissue growth in or from the abdominal region. It is also contemplated that the term may be used to refer to other similar tissue growths in the abdominal region, whether comprised of fat or other types of cells. The pannus may be typically located in the lower abdominal area, although other areas are possible. The pannus may impede the individual's motion by its weight or by its location. The limitations on motion may compound the individual's health issues by preventing exercise. It may also prevent the individual from engaging in other activities. In some severe cases, the pannus may prevent the individual from engaging in even routine activities such as getting out of bed, getting dressed, walking to the bathroom, leaving their house or dwelling, going to work, and the like.

Thus, an effective apparatus, system and method for limiting the restriction on motion caused by an abdominal panniculus would be well received in the art.

SUMMARY

According to one embodiment, a pannus support device comprises: a pannus pouch configured to receive an abdominal panniculus of a wearer that is extending to cover at least a portion of the thigh; a shoulder support structure; and at least one strap connecting the pannus pouch to the shoulder support structure; wherein the shoulder support structure, the at least one strap and the pannus pouch are configured to distribute the weight of the abdominal panniculus to the shoulders of the wearer and off at least the portion of the thigh of the wearer.

According to another embodiment, a method of supporting a pannus comprises: providing a pannus support device that includes: a pannus pouch; a shoulder support structure; and at least one strap connecting the pannus pouch to the shoulder support structure; receiving, by the pannus pouch, an abdominal panniculus of a wearer; distributing weight, by the pannus support device, of the abdominal panniculus to the shoulders of the wearer; and removing the weight of the abdominal panniculus from at least a portion of a thigh of the wearer.

According to another embodiment, a pannus support system comprises: a pannus pouch configured to receive an abdominal panniculus of a wearer that is extending to cover a thigh of the wearer; a shoulder support structure; at least one strap connecting the pannus pouch to the shoulder support structure; and a removable pannus pouch liner located in the pannus pouch; wherein the shoulder support structure, the at least one strap and the pannus pouch are configured to distribute the weight of the abdominal panniculus to the shoulders of the wearer and off the thigh.

BRIEF DESCRIPTION OF THE DRAWINGS

The subject matter which is regarded as the invention is particularly pointed out and distinctly claimed in the claims included at the conclusion of this specification. The foregoing and other features and advantages of the invention are apparent from the following detailed description taken in conjunction with the accompanying drawings in which:

FIG. 1 depicts a front perspective view of a pannus support device in accordance with one embodiment; and FIG. 2 depicts a rear perspective view of the pannus support device of FIG. 1 in accordance with one embodiment;

FIG. 3 depicts a front perspective view of the pannus support device of FIG. 1-2 being worn by a wearer in accordance with one embodiment;

FIG. 4 depicts a rear perspective view of the pannus support device of FIG. 1-3 being worn by a wearer in accordance with one embodiment;

DETAILED DESCRIPTION

Figure 6:
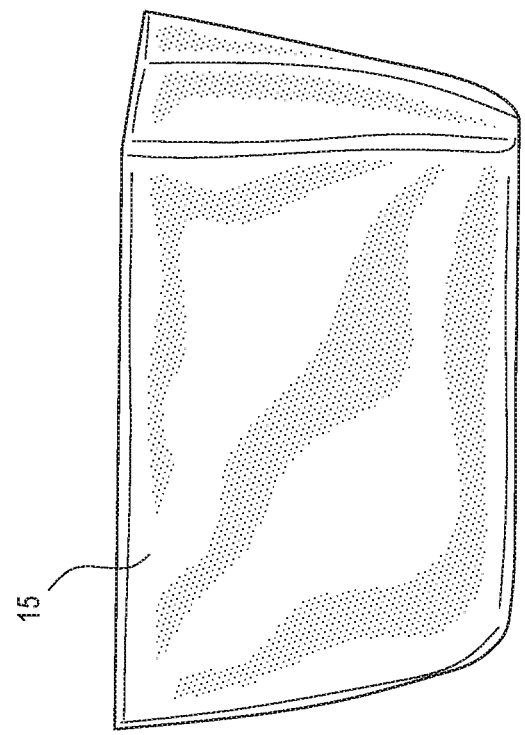
FIG. 6 depicts a pouch liner that is insertable into a pannus pouch of the pannus support device of FIG. 1-5 in accordance with one embodiment.

Although certain embodiments of the present invention will be shown and described in detail, it should be understood that various changes and modifications may be made without departing from the scope of the appended claims. The scope of the present invention will in no way be limited to the number of constituting components, the materials thereof, the devices thereof, the relative arrangement thereof, etc.; these are disclosed simply as an example of an embodiment. The features and advantages of the present invention are illustrated in detail in the accompanying drawings, wherein like reference numerals refer to like elements throughout the drawings.

As a preface to the detailed description, it should be noted that, as used in this specification and the appended claims, the singular forms "a", "an" and "the" include plural referents, unless the context clearly dictates otherwise.

Referring first to FIGS. 1-2, an embodiment of a pannus support device 100 for supporting a pannus or abdominal panniculus is shown. In one embodiment, the pannus support device 100 may be constructed and situated so that it redistributes the weight of the pannus or panniculus from an individual's legs or waist. Further, in one embodiment, the pannus support device 100 may be constructed and situated so that the physical location of the pannus or panniculus is changed. For example, the pannus or panniculus may be lifted away from the user's legs or waist to prevent the pannus or panniculus from interfering with the individual's movement.

In one embodiment, the pannus support device 100 comprises a pannus pouch 10. The pannus pouch 10 may be capable of receiving and supporting a pannus or panniculus (not shown) of an individual 200. The pannus pouch 10 may be comprised of a fabric such as cotton, polyester, canvas, denim, corduroy, and the like. A blend of two or more fabrics may also be used. In one embodiment, the pannus pouch 10 may be a blended fabric material. In a further embodiment, more rigid materials may be used such as plastic, wood, metal, a composite and the like may be used to for the pannus pouch 10. Still further, the rigid materials may be covered or lined with fabric or other softer material.

In one embodiment, substantially inelastic fabric materials may be used to form the pannus pouch 10. Substantially inelastic may mean that the fabric material is not prone to stretching or expanding when subjected to the weight of a pannus or panniculus. This is in contrast to an elastic or formfitting material such as spandex, lycra, elastane and the like. For example, in one embodiment, the pannus pouch 10 may be formed of a material strong enough to support twenty five to fifty pounds without deformation of the pannus pouch 10. In a further embodiment, the pannus pouch 10 may support even more weight, for example weight up to and exceeding one hundred pounds. In one embodiment, the pannus pouch 10 may be capable of supporting such weight so that the force of the weight is redistributed to the individual's shoulders and is lifted away from the user's legs. In one embodiment, the pannus pouch 10 may be capable of supporting weight so that the force of the weight is redistributed to the shoulders of a wearer 200 and off a thigh of the wearer 200, shown in FIGS. 3-5. The pannus pouch 10 may be capable of supporting weight so that the force of the weight is redistributed to the shoulders of the wearer 200 and off the genetalia, thigh, upper thigh, mid-thigh or knees of the wearer 200.

In one embodiment, the pannus support device 100 may include only a single pannus pouch 10. In further embodiments, additional pannus pouches 10 may be included. The additional pannus pouches 10 may be located next to or adjacent to each other, may be spaced apart, or may be placed at varying points (i.e., at the individual's front, sides, back, etc.).

The pannus pouch 10 may have a front side 11 and a back side 12 with a space 13 between the front side 11 and the back side 12 for receiving the individual's pannus or panniculus. Side panels 14 may be used to connect the front side 11 with the back side 12. In other embodiments, the front side 11 and the back side 12 may connect directly without the need for the side panels 14 (shown in FIGS. 7-8).

In one embodiment, the support system 100 may include a set of front straps 20. A set of back straps 30 may also be included in one embodiment. In one embodiment, a set of front straps 20 and a set of back straps 30 may mean that there are two front straps 20 and two back straps 30. Further, in one embodiment, the front straps 20 may be positioned such that there is one front strap 20 on each side of the pannus pouch 10, i.e., one front strap 20 for each of the individual's shoulders. In one embodiment, a similar structure may be adopted for the back straps 30. The front straps 20 and back straps 30 may be made of any suitable material. In one embodiment, the front straps 20 and back straps 30 may be made of the same material as the pannus pouch 10; in a further embodiment, they may be formed of a different material or a different blend of materials. In one embodiment, the front straps 20 and the back straps 30 are made from a substantially inelastic material, as defined hereinabove. The use of an inelastic material may provide support for the weight of the pannus without stretching or deforming the shape of the pannus support device 100.

In one embodiment, the front straps 20 and back straps 30 may be attached to the pannus pouch 10 by a variety of means, such as stitching, hook and loop fasteners, buttons, snaps, fasteners, buckles and the like. In the embodiment shown, the front and back straps 20, 30 may be permanently attached into the pannus pouch 10 via stitching. In other embodiments, the front and back straps 20, 30 may be more easily and/or attachably removable to facilitate in a person donning or removing the pannus support device 100. In one embodiment, one side (left or right) may include a removable strap while the other side may include a permanently stitched or attached strap. In another embodiment, at least two of the front straps 20, the back straps 30, and the pannus pouch 10 may be made of one continuous piece of material.

In a further embodiment, the front straps 20 and the back straps 30 may be adjustable. In one embodiment the front straps 20 and the back straps 30 may be adjusted by slide buckles 45. Other adjustment mechanisms are contemplated, such as hook and loop fasteners or holes located in the straps 20, 30 to correspond with a bar and tongue style buckle.

In one embodiment, the front straps 20 and the back straps 30 may connect to a shoulder support structure 40. In one embodiment, the shoulder support structure 40 may be configured to rest on the individual's shoulders. In one embodiment, the shoulder support structure 40 may include a shoulder support portion 41 for each of the individual's shoulders. In a further embodiment, the shoulder support structure 40 may also include a chest harness portion 42 and/or a back harness portion 43. The chest harness portion 42 and the back harness portion 43 may connect to the shoulder support portions 41. In a further embodiment, the chest harness portion 42 may connect to each of the front straps 20 and may be positioned between the front straps 20. Similarly, in one embodiment, the back harness portion 43 may connect to each of the back straps 30 and may be positioned between the back straps 30.

Figure 5:
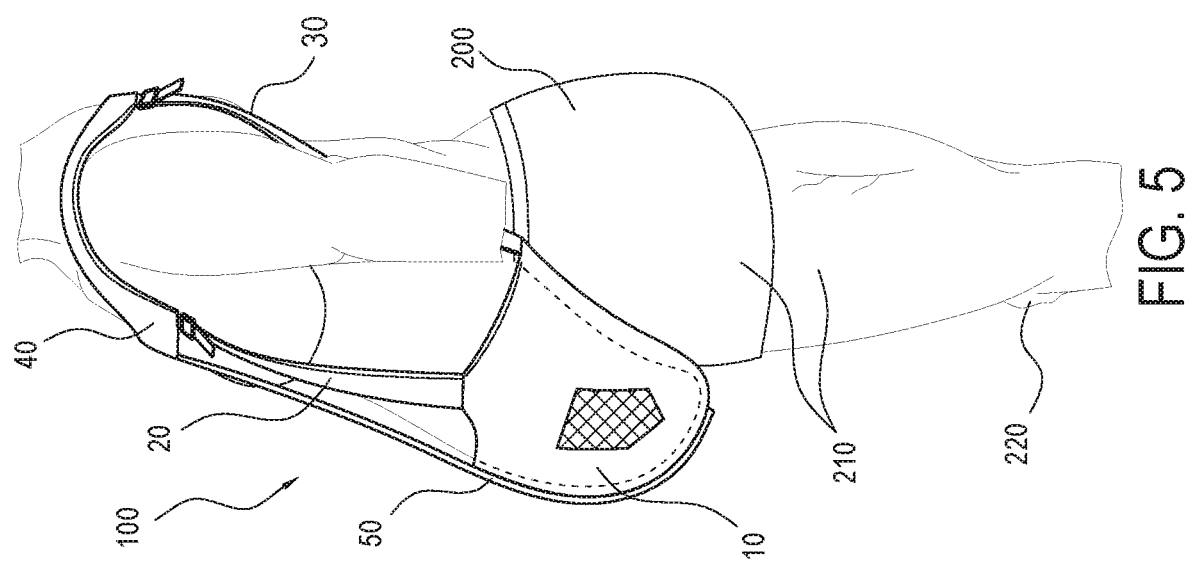
FIG. 5 depicts a side perspective view of the pannus support device of FIG. 1-4 being worn by a wearer in accordance with one embodiment.

As shown in FIGS. 3-5, the pannus pouch 10 may be configured to receive the abdominal panniculus of the wearer 200 that is extending to cover the thigh 210, or even the knees 220, of the wearer 200 prior to being received and supported by the pannus pouch 10. The shoulder support structure 40, the straps 20, 30 and the pannus pouch 10 may be configured to distribute the weight of the abdominal panniculus to the shoulders of the wearer 200 and off at least the portion of the thigh 210 of the wearer 200, as shown in FIGS. 3-5. The shoulder support structure 40, the straps 20, 30 and the pannus pouch 10 may be configured to distribute the weight of the abdominal panniculus to the shoulders of the wearer 200 and off the middle of the thigh 210 of the wearer or the knees 220 of the wearer. The thickness and strength of the material of the straps 20, 30, the pouch 10 and the shoulder support structure 40 may be appropriately adjusted depending on the weight that the pannus support device 100 is required to hold.

Similar to the front straps 20 and back straps 30, the shoulder support portions 41, chest harness portion 42, and back harness portion 43, may all be made of the same material or may be formed as one continuous piece of material. In another embodiment, one or more of these elements may formed from a different material or different blend of materials. Each of these portions may be made from different pieces of material to increase the adjustability of the pannus support device 100. In one embodiment, the components of the shoulder support structure 40 and the shoulder support structure 40 may be substantially inelastic, as has been described. The substantially inelastic quality may provide support for the weight of the pannus without stretching or deforming the shoulder support structure 40 or its components. In one embodiment, the components of the shoulder support structure 40 may retain the substantially inelastic quality while being adjustable.

Further, the shoulder support structure 40, the straps 20, 30 and the pannus pouch 10 may be configured to evenly distribute the weight of the abdominal panniculus across the shoulders and back area. This may be accomplished with the straps 20, 30 on both sides of the shoulder support structure 40 having a bib-like structure having the back harness portion 43 thick and pulled tight through the back straps 30 when the weight is being held.

The shoulder support structure 40 may include padding (not shown). The padding may be located on the entirety of the shoulder support structure 40 or may be located only on an underside of the shoulder support structure 40, that is, the side which would contact the individual or their clothing. In one embodiment, the padding may be included on the shoulder support portion 41, the chest harness portion 42, the back harness portion 43, or any combination of these elements. The padding may serve to cushion the weight of the pannus that is being transferred to the shoulders.

In a still further embodiment, the connection between the components of the shoulder support structure 40, that is the shoulder support portions 41, the chest harness portion 42, and the back harness portion 43, may be adjustable. In particular, one or more of the front straps 20, the back straps 30, the shoulder support portions 41, the chest harness portion 42, and the back harness portion 43 may be expandable or contractible. Adjustment of these features may be accomplished by a variety of means, such as an adjustable buckle; a plurality of buttons, snaps, or other fasteners; or the like. In the embodiment shown, additional material from the chest harness portion 42 may extend into the shoulder support portions 41. This material may be removed from the chest harness portion 42 in order to expand the dimensions of the shoulder support structure 40. While it is now shown in the Figures, this same concept may be applied to the back harness portion 43.

In one embodiment, the back straps 30 may be configured to extend downward in a substantially vertical fashion from the connection (at an upper portion of the back strap 30) to the back harness portion 43, shoulder support structure 40, and/or the front strap 20. Substantially vertical fashion may mean directly down, without a crossing pattern. In one embodiment, the back straps 30 are connected directly to the pannus pouch 10 at a lower portion of the back strap 30. Further, in one embodiment, the direct connection of the back straps 30 to the pannus pouch 10 may facilitate the transfer of weight directly to the shoulders, rather than to the waist or back.

In one embodiment, the pannus support device 100 may include a support strap 50. The support strap 50 may attach to both the pannus pouch 10 and the shoulder support structure 40. For example, the support strap 50 may attach to the front of the pannus pouch 10 at one end, and attach to the chest harness portion 42 at its other end. The support strap 50 may be made of the same material as the pannus pouch 10 and/or the front straps 20, the back straps 30, the shoulder support portions 41, the chest harness portion 42, and the back harness portion 43. In one embodiment, the support strap 50 may be attached to the pannus pouch 10 and/or the shoulder support structure 40 by any of the connection means discussed herein. In a further embodiment, the support strap 50 may be formed of one continuous piece of material along with the pannus pouch 10 and/or the shoulder support structure 40. In one embodiment, a plurality of support straps 50 may be used to provide additional support for the pannus pouch 10. Still further, in one embodiment, the support strap 50 may be formed of a substantially inelastic material as defined hereinabove. The use of a substantially inelastic material may facilitate the redistribution of weight to the shoulders, while preventing stretching or deformation of the pannus support device 100. The support strap 50 may be attached to the shoulder support structure 40 or the chest harness portion 42 of the shoulder support structure 40 in an adjustable fashion (not shown). Thus, the length of the support strap 50 may be adjustable to provide more or less support for the wearer 200 or to change the setting if the wearer loses or gains weight.

In one embodiment, the pannus pouch 10 may be configured to lift the weight of the pannus when the pannus is placed in the pannus pouch 10 and the support system 100 is in use. For example, when in use, the individual may place the pannus support device 100 over the individual's head, so that the shoulder support structure 40 passes over the head, around the neck, and rests on the individual's shoulder area. In one embodiment, the pannus support device 100 may be placed so that the pannus pouch 10 is located at the front of the individual 200. In another embodiment, the pannus support device 100 may be placed so that the pannus pouch 10 is located at the rear of the individual 200. In a still further embodiment, the pannus support device 100 may include a plurality of pannus pouches 10; the individual pannus pouches 10 may be located at varying points around the individual 200.

When the pannus support device 100 is to be used and is placed on the individual's body, the pannus or panniculus may be lifted and placed into the pannus pouch 10. In one embodiment, the weight of the pannus may then be redistributed from the individual's waist and legs and onto the shoulders. In yet another embodiment, placement of the pannus into the pannus pouch 10 may also lift the pannus away from the individual's legs allowing a greater range of motion. This adjustment of the pannus may remove an impediment to ambulation and movement. In one embodiment, the pannus support device 100 may thus increase the individual's ability to walk and exercise, thereby leading to a potential improvement in health and wellness.

In a further embodiment, the pannus support device 100 may include a pannus pouch liner 15, shown in FIG. 6. Thus, the pannus support device 100 and one or more of the pannus pouch liners 15 may be provided together as a pannus support system. In one embodiment, the pannus pouch liner 15 may be a pad that can be placed in the pouch to prevent direct contact between the individual's pannus or panniculus and the material of the pannus pouch 10. In one embodiment, the pannus pouch liner 15 may be comprised of sterile or non-sterile gauze, cotton gauze, a cotton pad, and the like. In a further, embodiment, the pannus pouch liner 15 may also be impregnated with or treated with medication such as zinc oxide, calamine lotion, acacia, glycerin, castor oil, white petroleum, antibacterial ointment, and other medications. The impregnated or treated pannus pouch liner 15 may be used for the treatment or relief of certain conditions. For example, in one embodiment, the impregnated or treated pannus pouch liner 15 may be used to treat or relieve the symptoms of ulcers, pressure sores, and the like. In a further embodiment, the pannus pouch line 15 may contain substances for preventing infection or bacterial growth.

In a still further embodiment, the pannus pouch 10 may include pockets 16. The pockets 16 may be configured to receive and/or store an object or objects. For example, in one embodiment, the individual 200 may have medical devices (not shown) attached to their body as a result of a medical condition, such as medical or surgical drains or other devices. The pockets 16 may receive and store these medical devices to keep them from interfering with the individual's movement. The pockets 16 may also be used for storage of other objects. In one embodiment, the pockets 16 may be a single enlarged pocket extending along the outside of the front side 11 of the pannus pouch 10. Any number, sizes and location of pockets are contemplated. The pockets 16 may be made from an elastic mesh material.

Figure 8:
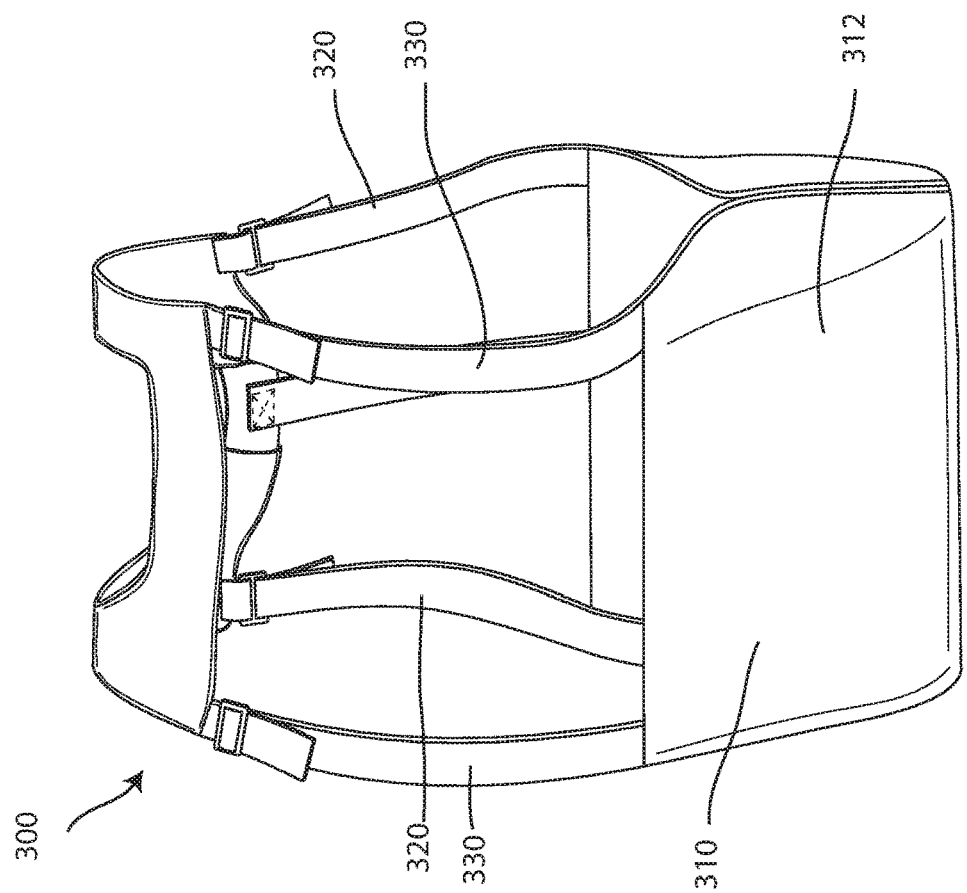
FIG. 8 depicts a rear perspective view of the pannus support device of FIG. 7 in accordance with one embodiment.
Figure 7:
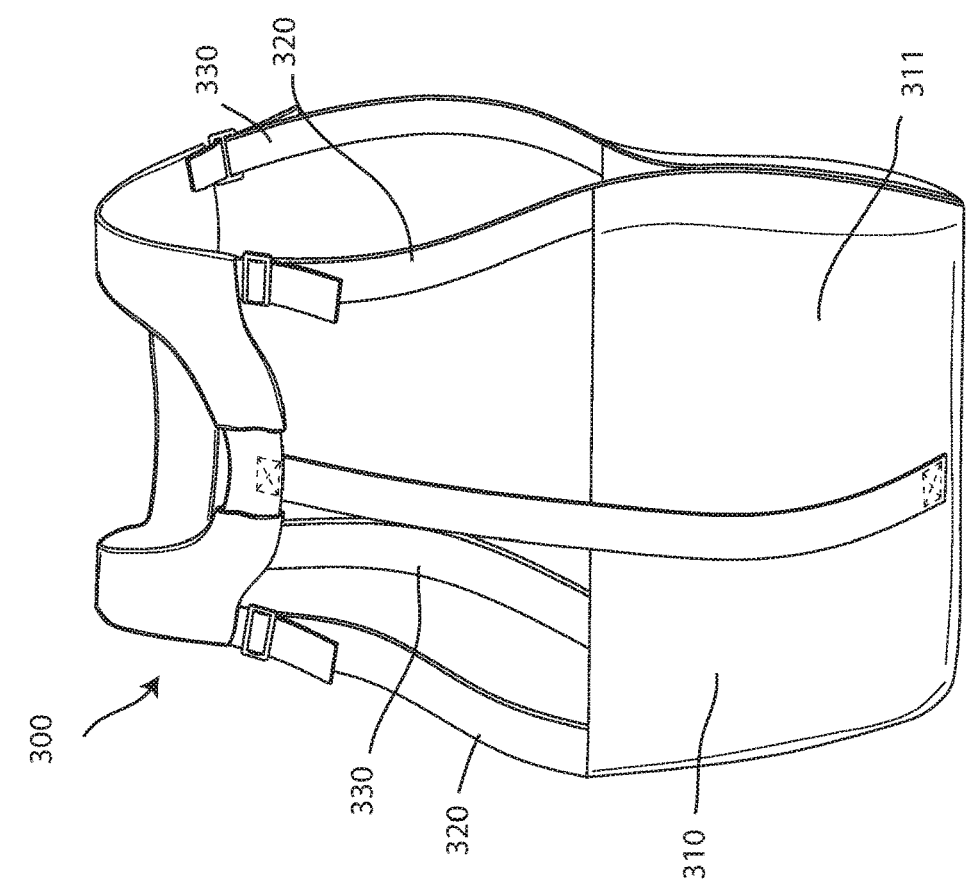
FIG. 7 depicts a front perspective view of another pannus support device in accordance with one embodiment.

Referring now to FIGS. 7-8 another pannus support device 300 is shown. The pannus support device 300 may be the same or similar to the pannus support device 100. However, the pannus support device 300 may include a pannus pouch 310 having a front side 311 and a back side 312 that are connected directly without the need for side panels. This may be configured to allow the corresponding front straps 320 and back straps 330 to converge to the pannus pouch 310 at a similar location on the pannus pouch 310 without space therebetween. Like the previous embodiment, this embodiment may also ensure that the straps 320, 330 are pulling up the abdominal panniculus off the legs, thighs and/or knees of the wearer in an even manner.

Further disclosed herein is a method of supporting a pannus as shown in FIGS. 3-5 that includes providing a pannus support device, such as the pannus support device 100, that includes a pannus pouch, such as the pannus pouch 10, a shoulder support structure, such as the shoulder support structure 40, and at least one strap connecting the pannus pouch to the shoulder support structure 40, such as the straps 20, 30. The method may include receiving, by the pannus pouch, an abdominal panniculus of a wearer, such as the wearer 200. The method may include distributing weight, by the pannus support device, of the abdominal panniculus to the shoulders of the wearer. The method may include removing the weight of the abdominal panniculus from at least a portion of a thigh of the wearer. Further, the method may include removing the weight of the abdominal panniculus from a middle of the thigh of the wearer. Still further the method may include removing the weight of the abdominal panniculus from the knees of the wearer. These removing steps may be accomplished by redistributing the weight from the thigh or knees to the shoulders of the wearer. The method may further include applying a pannus pouch liner, such as the liner 15, to the pannus pouch. The pannus pouch liner may be applied to the abdominal panniculus region of the wearer before the pannus support device is applied. The wearer may enclose or encircle their abdominal panniculus with the pannus pouch, and then do the same with the pannus pouch. Once the pannus pouch is in position, the wearer may place a shoulder support structure 40 over their head with unattached straps and/or hanging straps, such as the front straps 20 and the rear straps 30. The unattached straps may finally be attached to the pannus pouch in the manner shown in either FIG. 1-2 or 7-8, and then the attached straps, and a support strap, such as the support strap 50, may be adjusted.

Elements of the embodiments have been introduced with either the articles "a" or "an." The articles are intended to mean that there are one or more of the elements. The terms "including" and "having" and their derivatives are intended to be inclusive such that there may be additional elements other than the elements listed. The conjunction "or" when used with a list of at least two terms is intended to mean any term or combination of terms. The terms "first" and "second" are used to distinguish elements and are not used to denote a particular order.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A pannus support device comprising:
   a pannus pouch configured to receive an abdominal panniculus of a wearer that is extending to cover at least a portion of a thigh of the wearer;
   a shoulder support structure; and
   at least one strap connecting the pannus pouch to the shoulder support structure;
   wherein the pannus pouch and the at least one strap are made from an inelastic fabric;
   wherein the shoulder support structure, the at least one strap and the pannus pouch are configured to distribute a weight of the abdominal panniculus to the shoulders of the wearer and off at least the portion of the thigh of the wearer;
   wherein the at least one strap includes:
      two front straps extending substantially vertically from a front side of the pannus pouch directly to a front side of the shoulder support structure; and
      two back straps extending substantially vertically from a back side of the pannus pouch directly to a back side of the shoulder support structure.

2. The pannus support device of claim 1,
   wherein the two front straps and the two back straps are adjustable.

3. The pannus support device of claim 1, further comprising a support strap extending from a chest portion of the shoulder support structure to a lower middle portion of the pannus pouch.

4. The pannus support device of claim 1, wherein the pannus pouch is configured to receive the abdominal panniculus of the wearer that is extending to cover a middle of the thigh of the wearer, and wherein the shoulder support structure, the at least one strap and the pannus pouch are configured to distribute the weight of the abdominal panniculus to the shoulders of the wearer and off the middle of the thigh of the wearer.

5. The pannus support device of claim 1, wherein the pannus pouch is configured to receive the abdominal panniculus of the wearer that is extending to cover the knees of the wearer, and wherein the shoulder support structure, the at least one strap and the pannus pouch are configured to distribute the weight of the abdominal panniculus to the shoulders of the wearer and off the knees of the wearer.

6. The pannus support device of claim 1, wherein the shoulder support structure includes two shoulder support portions connected by a back harness portion extending between the two shoulder portions on a back side, the two shoulder support portions further connected by a chest portion extending between the two shoulder portions on a front side.

7. The pannus support device of claim 6, wherein the shoulder support structure is adjustable in size.

8. The pannus support device of claim 1, further comprising a removable pannus pouch liner located in the pannus pouch.

9. The pannus support device of claim 1, wherein the pannus support device further includes at least one pocket on an exterior, the at least one pocket configured to receive a medical device.

10. A method of supporting a pannus comprising:
providing a pannus support device that includes:
a pannus pouch;
a shoulder support structure; and
at least one strap connecting the pannus pouch to the shoulder support structure,
wherein the pannus pouch and the at least one strap are made from an inelastic fabric, and wherein the at least one strap includes:
two front straps extending substantially vertically from a front side of the pannus pouch directly to a front side of the shoulder support structure; and
two back straps extending substantially vertically from a back side of the pannus pouch directly to a back side of the shoulder support structure;
receiving, by the pannus pouch, an abdominal panniculus of a wearer;
distributing weight, by the pannus support device, of the abdominal panniculus to the shoulders of the wearer; and
removing the weight of the abdominal panniculus from at least a portion of a thigh of the wearer.

11. The method of claim 10, further comprising:
removing the weight of the abdominal panniculus from a middle of the thigh of the wearer.

12. The method of claim 10, further comprising:
removing the weight of the abdominal panniculus from the knees of the wearer.

13. A pannus support system comprising:
a pannus pouch configured to receive an abdominal panniculus of a wearer that is extending to cover a thigh of the wearer;
a shoulder support structure;
at least one strap connecting the pannus pouch to the shoulder support structure; and
a removable pannus pouch liner located in the pannus pouch;
wherein the pannus pouch and the at least one strap are made from an inelastic fabric;
wherein the at least one strap includes:
two front straps extending substantially vertically from a front side of the pannus pouch directly to a front side of the shoulder support structure; and
two back straps extending substantially vertically from a back side of the pannus pouch directly to a back side of the shoulder support structure;
wherein the shoulder support structure, the at least one strap and the pannus pouch are configured to distribute a weight of the abdominal panniculus to the shoulders of the wearer and off the thigh.

14. The pannus support device of claim 13, wherein the two front straps and the two back straps are adjustable.

15. The pannus support system of claim 13, further comprising a support strap extending from a chest portion of the shoulder support structure to a lower middle portion of the pannus pouch.

16. The pannus support system of claim 13, wherein the shoulder support structure includes two shoulder support portions connected by a back harness portion extending between the two shoulder portions on a back side, the two shoulder support portions further connected by a chest portion extending between the two shoulder portions on a front side.

17. The pannus support system of claim 16, wherein the shoulder support structure is adjustable in size.

18. The pannus support system of claim 13, wherein the pannus support pouch further includes at least one pocket on an exterior, the pannus support pouch configured to receive a medical device.

* * * * *